United States Patent [19]
Nevins

[11] 3,968,567
[45] July 13, 1976

[54] ENDODONTIC COMPOSITION AND METHOD

[76] Inventor: Alan J. Nevins, 200 Carmen Ave., Apt. 7C, East Meadow, N.Y. 11554

[22] Filed: Apr. 21, 1975

[21] Appl. No.: 569,675

[52] U.S. Cl. .......................................... 32/15; 3/1; 106/161
[51] Int. Cl.² ......................................... A61K 5/01
[58] Field of Search ....................... 32/15, 1; 128/1; 106/149, 161; 3/1 R

[56] References Cited
UNITED STATES PATENTS

| | | | |
|---|---|---|---|
| 3,443,261 | 5/1969 | Battista et al. | 3/1 |
| 3,679,360 | 7/1972 | Rubin et al. | 23/109 |
| 3,742,955 | 7/1973 | Battista et al. | 106/161 X |
| 3,767,437 | 10/1973 | Cruz, Jr. | 106/161 |

OTHER PUBLICATIONS

Steiner et al., Experimental Root Apexification in Primates, *Oral Surgery*, 31:409–415, May, 1971.
Ham et al., Induced Apical Closure of Immature Pulpless Teeth in Monkeys, *Oral Surgery*, 33:438–449, Mar., 1972.
Dylewski, Apical Closures of Non–Vital Teeth, *Oral Surgery*, 32:82–89, July 1971.
Narang et al., Experimental Osteogenesis in Periapical Areas with Decalcified Allogeneic Bone Matrix, *Oral Surgery*, 35:136–143, Jan., 1973.
Lutwak et UCLA Conference, Current Concepts of Bone Metabolism, *Annals of Internal Medicine*, 80:630–644, May, 1974.
Van De Putte et al., Osteogenesis in the Interior of Intramuscular Implants of Decal Bone Matrix, *Clinical Orth and Related Res.*, 43:270, 1955.
Nimmi: Metabolic Pathways and Control Mech. Involved in the Biosyn. and Turnover of Collagen . . ., *J. Oral Path.*, 2:175, (1973).
Termine et al., Calcium Phosphate Formation in Vitro, *Arch. of Brochem. and Biophysics*, 140:307, (1970).
Torneck, Reaction of Rat Connection Tissue to Polyethylene Tube Implanting, *Oral Surg., Oral Med. and Oral Path.*, 21:379, (1966).
Chvapil et al., *International Rev. of Connective Tissue Res.*, vol. 6, Academic Press, N.Y., 1973.
Marondas, N. G., Chemical and Mechanical Requirements for Fiberblast Adhesion, *Nature*, 244:353, (1973).

*Primary Examiner*—Robert Peshock
*Assistant Examiner*—Jack Q. Lever
*Attorney, Agent, or Firm*—Brumbaugh, Graves, Donohue & Raymond

[57] ABSTRACT

A composition useful in forming a physiologic root end closure, a method of making the composition and a method utilizing the composition. The composition comprises a buffered solution of colloidal collagen, a calcium salt, a phosphate salt, and optionally, Lugol's solution.

20 Claims, 4 Drawing Figures

ENDODONTIC COMPOSITION AND METHOD

BACKGROUND OF THE INVENTION

The present application relates to an endodontic composition useful for forming a physiologic root end closure in pulpless endodontically treated teeth, including non-vital open apex teeth, and to a method for stimulating formation of said closure using said composition. More particularly, the composition of the invention comprises a buffered collagen gel containing a calcium salt and a phosphate salt. Lugol's solution may be added to the composition to speed gellation.

Various techniques have been advocated for endodontic treatment of non-vital open apex teeth. Most root canals in need of such treatment are irregularly shaped. Thus, techniques using solid or semi-solid root canal fillings, such as silver points, gutta percha cones, and various cements usually leave voids between the filling and the canal wall. Since much of the success of endodontics depends upon an adequate sealing of the apical portion of the root canal, voids must be prevented because canals with no filling material or partially filled canals tend to accept tissue fluids through the apical foramen and become infected.

Another previously used technique makes use of root canal pastes, such as calcium hydroxide-camphorated parachlorophenol paste. Pastes do obviate the problem of voids. However, conventional paste materials, when in contact with periapical tissues and tissue fluids, tend to resorb. They also may stimulate cytotoxic and antigenic inflammatory reactions. These problems are pronounced in non-vital open apex teeth with canals of flaring morphology, and because of the large surface of periapical tissues contactng the root canal filling material. Also, growth of connective tissue into the root canal is usually limited to less than one millimeter and bridging of the apex with calcification is usually incomplete.

The apexification usually occurs slowly where calcium hydroxide is used to induce hard tissue closure of root canal openings and is often incomplete as described in the article by Steiner, J. C., and Van Hassel, J. J.: Experimental Root Apexification in Primates, *Oral Surgery* 31:409 (1971). An 18 month treatment period is considered by the authors to be an adequate length of time for a satisfactory apical closure. Another group of workers in the field demonstrated that this type of bridging is porous and concluded that a permanent root canal filling should eventually be placed to form a complete seal; see Ham, J. W. Paterson, S. S. and Mitchell, D. F.: Induced Apical Closure of Immature Pulpless Teeth in Monkeys, *Oral Surgery* 33:438 (1972). Other research indicated that repair at the apex constitutes proliferation of connective tissue with eventual differentiation into a hard tissue bridge; see Dylewski, J. J.: Apical closures of Non-Vital Teeth, *Oral Surgery* 32:82 (1971).

Still another technique advocated is that of pushing instruments through the apical foramen to stimulate bleeding into the root canal. The resulting clot formation serves as a matrix for connective tissue and capillary ingrowth. Again, ingrowth is usually limited to less than one millimeter and bridging of the apex with calcified material is incomplete.

Another problem with the prior art methods comes from the fact that the canal is divergent toward the apex. This condition makes it very difficult to adequately clean and smooth the walls with instruments. The difficulty in cleansing can result in bacterial contamination existing in the canal at the time the tooth is filled, and bacterial growth under these conditions is known to inhibit apical closure.

In another approach to this problem, decalcified allogenic bone matrix grafts were surgically implanted into root canals and periapical areas of teeth in monkeys. Formation of new cementum within the canals and new bone within the surgically formed bone cavities was observed. While this technique is of interest, it has the drawback that (1) a surgical procedure is required, (2) it requires the use of non-purified material, and (3) the implant does not conform to the shape of the canal.

The bone morphogenic property of decalcified bone matrix has been well-established; see Narang, R. and Wells, H.: Experimental Osteogenesis in Periapical Areas with Decalcified Allogenic Bone Matrix, *Oral Surgery* 35:136 (1973). The collagen component of the implant is thought to contribute significantly to the osteogenic response. Mesenchymal cells of the recipient tissue migrate to the implant, palisade, and differentiate into osteoblasts, which in turn produce new bone; see Lutwak, L., Singer, F. R. and Urist, M. R.: UCLA Conference, Current Concepts of Bone Metabolism, *Annals of Internal Medicine*, 80, (1974) and Van de Putte, K. A. and Urist, M. R.: Osteogenesis in the Interior of Intramuscular Implants of Decalcified Bone Matrix, *Clinical Orthopaedics and Related Research* (edited by DePalma, A. F.) Vol. 43, 270, (J. B. Lippincott Co., Phil. 1965).

Skin derived collagen and bone matrix collagen appear to be similar both structurally and chemically; see Nimmi, M. E., Metabolic Pathways and Control Mechanisms Involved in the Biosynthesis and Turnover of Collagen in Normal and Pathological Connective Tissues, *J. Oral Path.* 2:175 (1973). Skin derived collagen sponges have been implanted into debrided osteomyelitic infection sites resulting in accelerated wound healing; see Chvaoil, M., Kronenthal, R. L., and Van Winkle, W., Jr.: Internat Rev. of Conn. Tissue Res. (edit. by Hall, D. A., and Jackson D. S.) Vol. 6: (Academic Press, N.Y. 1973). Skin derived collagen has also been used with $CaCl_2$ and $K_2HPO_4$ to form hydoxyapatite crystals; see Termine, J. D., and Posner, A. S., Calcium Phosphate Formation in Vitro, *Arch. of Biochem. and Biophysics* 140, 307 (1970). In vitro studies have demonstrated the dynamics of fibroblast migration along the micro-scaffold provided by the fibrils within a collagen gel; see Maroudas, N. G.: Chemical and Mechanical Requirements for Fibroblast Adhesion, *Nature*, 244, 353 (1973).

SUMMARY OF THE INVENTION

There is provided, in accordance with the present invention, a method for causing formation of a physiologic seal across the opening of a rigid tubular member adjacent capsular connective tissue within a mammalian body comprising the steps of filling the tube with a gelable composition comprising collagen, a calcium salt and a phosphate salt, allowing the composition to gel and permitting the ingrowth of connective tissue into the cavity. More particularly, the invention provides an endodontic composition and method useful for physiologic root canal closure of pulpless endodontically treated teeth, including non-vital open apex teeth. The composition may also serve as a matrix for new bone formation to fill the cavities of dental cysts and other bony defects. While the composition of the invention comprises a collagen solution containing a calcium salt and phoshate salt, it may also include a small amount of Lugol's solution to speed gelation and to act as an antiseptic.

The pulp canal of the tooth is prepared for treatment according to the present invention by first mechanically or chemically excising and removing dead and devitalized tissue from the canal. Where an abscess is present in the periapical tissue, it is drained, cleaned, and treated with antiseptic in the conventional manner, if desired. If the apical foramen is intact, it may be opened to permit access to periapical tissue from the debrided canal. This is particularly beneficial in those cases where the pulp is dead and access to healthy, living tissue is needed to form the physiologic seal.

After preparation of the canal and surrounding area, the endodontic composition of the present invention is syringed into the canal and into any abscess area which may be present in the periapical tissue. Care should be taken to leave no void spaces. The composition gels at body temperature, preferably within five to fifteen minutes. The tooth is sealed in the usual manner, e.g., by applying a gutta percha cone into approximately the first 4 mm. of the coronal portion of the root canal and then applying dental cement. Other equivalent methods of closing the coronal portion of the canal may be used.

Because of the nature of the composition of the present invention, there is no corrosion, and no voids form as with some of the prior art techniques. Also, the composition stimulates calcification and growth of connective tissue into the canal to a greater degree than any of the prior art techniques and in a much shorter time. The composition also avoids cytotoxic and antigenic reactions because it stimulates the body to heal itself rather than attempting to intrude with foreign materials.

The composition can also be used in pulpotomy and partial pulpectomy procedures. In these cases part of the pulp is still vital and the collagen-calcium phosphate composition is applied over the vital pulp to encourage bridging within the canal.

DETAILED DESCRIPTION OF THE INVENTON

The composition of the present invention may be conveniently prepared by combining and mixing three solutions in certain proportions. The first solution is prepared by reconstituting lyophilized, highly purified calf skin collagen in acetic acid with a pH of about 3–4, preferably pH 3.5, at a level of 10 mg. to 60 mg. of collagen per ml. of acetic acid. At a pH below 3, the acetic acid will denature the collagen, while at a pH above about 4, a sufficient amount of collagen will not solubilize. The resulting highly viscous solution is dialyzed against a phosphate buffer with a pH of from 7.4 to 7.6, preferably 7.6, at approximately 4°C for 24–48 hours. Dialysis is necessary to increase the pH of the collagen solution to physiologic pH. If the collagen solution is not to be used immediately, a preservative can be added to provide a stock collagen solution which is stored until needed.

A solution of $CaCl_2$ which may have a concentration ranging from 40 mM to 2.0 M is conveniently prepared in Tris buffer at a pH of 7.4. Similar solutions of $K_2HPO_4$ at concentrations ranging from 36 mM to 1.8 may be prepared in Tris buffer at pH 7.4. Tris is identified chemically as tris-(hydroxymethyl)-aminomethane, made by Sigma Co., St. Louis, Missouri, Order No. T-1503. Any other buffer with a physiologic pH, i.e., 7.4–7.6, will also be suitable in preparing the $CaCl_2$ and $K_2HPO_4$ solutions. A small quantity, in the order of 0.05 ml. per ml. of collagen solution, of 5% Lugol's solution may be used to speed gelation and to serve as an antiseptic. Lugol's solution contains 5 g. potassium iodide and 10 g. iodine per 100 ml. of solution.

The endodontic composition may be prepared by mixing the collagen, $CaCl_2$, $K_2HPO_4$ and Lugol's solutions just prior to use. The mole ratio of calcium to phosphate in the composition should be between 2:1 and 1:1 in order to simulate the theoretical ratio of calcium to phosphate in hydroxy apatite crystals. The resulting composition is a highly viscous material, and forms a gel within a half hour at 37°C.

Alternately, the solutions can be premixed and gelled in a container suitable for syringing the gelled preparation into the root canal. This technique for preparing the composition is especially useful for those compositions wth a high concentration of collagen, e.g. mixtures prepared by use of a 60 mg/ml collagen solution.

In accordance with another suitable technique for preparing the composition of this invention, the mixture of buffered collagen and salts is allowed to gel, and then centrifuged to remove the bulk of the precipitated salts. The remaining gel may be used where a high concentration of salts is undesired.

The invention will be further described with reference to the attached drawings in which.

Figure 1:
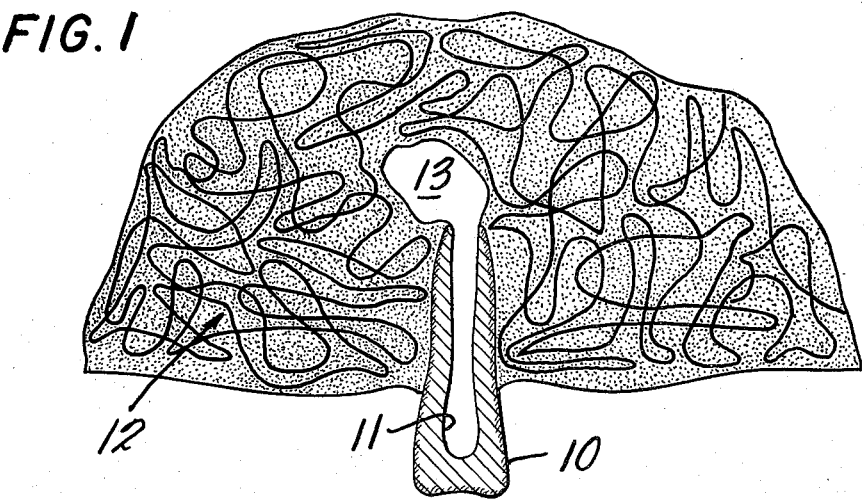
FIG. 1 is a diagrammatic representation of a pulpless endodontically treated tooth as may be treated in accordance with the invention showing an abscess in the periapical tissue.

Referring to the drawings, FIG. 1 shows a tooth 10, having a canal 11, and periapical tissue 12, having an abscess area 13. In accordance with the representation shown in FIG. 1, the canal 11 and abscess area 13 have been cleaned and drained and treated with antiseptic in preparation for further treatment.

Figure 2:
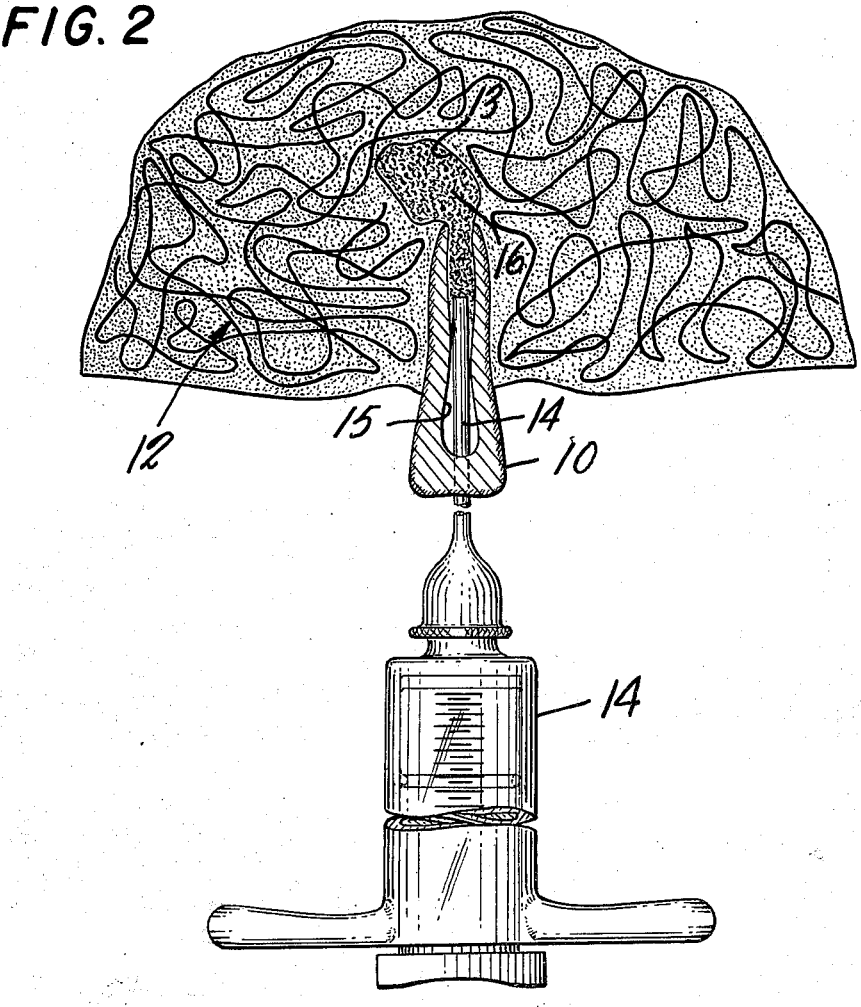
FIG. 2 is a similar diagrammatic showing of the gelable composition of the present invention as it is syringed into the canal and abscess area.
Figure 3:
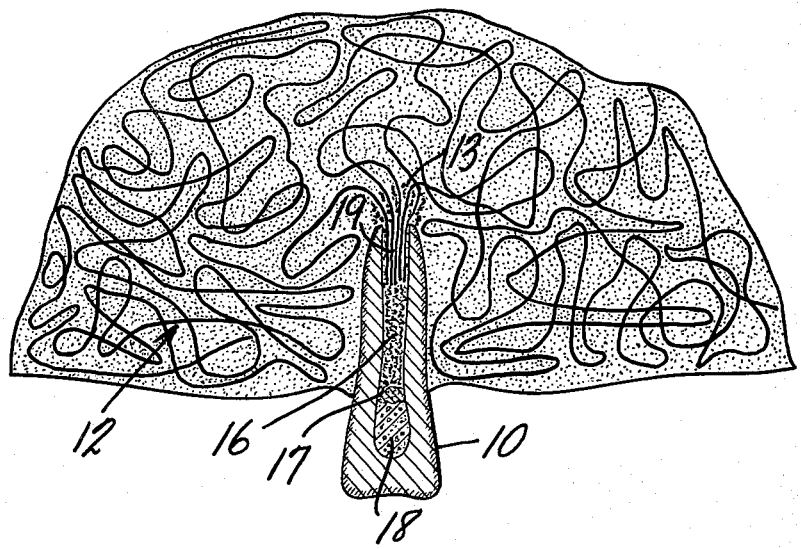
FIG. 3 is a diagrammatic representation showing the tooth of FIGS. 1 and 2 after partial healing of the abscess and partial ingrowth of connective tissue into the canal of the tooth.

In FIG. 2 of the drawings, the solutions containing collagen, $CaCl_2$, $K_2HPO_4$ and Lugol's solution as specifically described in Example 1 below, were thoroughly mixed and then syringed with a specially fitted straw-like syringe 14 with plunger into the debrided root canal 15. A sufficient amount of the collagen mixture 16 is inserted to fill the abscess area 13 as well as a portion of the canal 15 itself. The syringe is withdrawn and the mixture is then permitted to form a gel; gelation occurs within 5–15 minutes. The canal is then sealed in the usual manner by first applying a gutta percha cone 17 which extends approximately 4 mm. into the coronal portion of the root canal and then applying dental cement 18, as shown in FIG. 3. For a permanent filling, the usual amalgam is preferably applied over the cement 18.

After following the procedure outlined above, the abscess 13 heals rapidly due to the chemotactic attraction of fibroblasts by the collagen gel material. This is shown in the diagram in FIG. 3. FIG. also shows partial ingrowth of connective tissue 19 with fibroblasts into the canal of the tooth.

Figure 4:
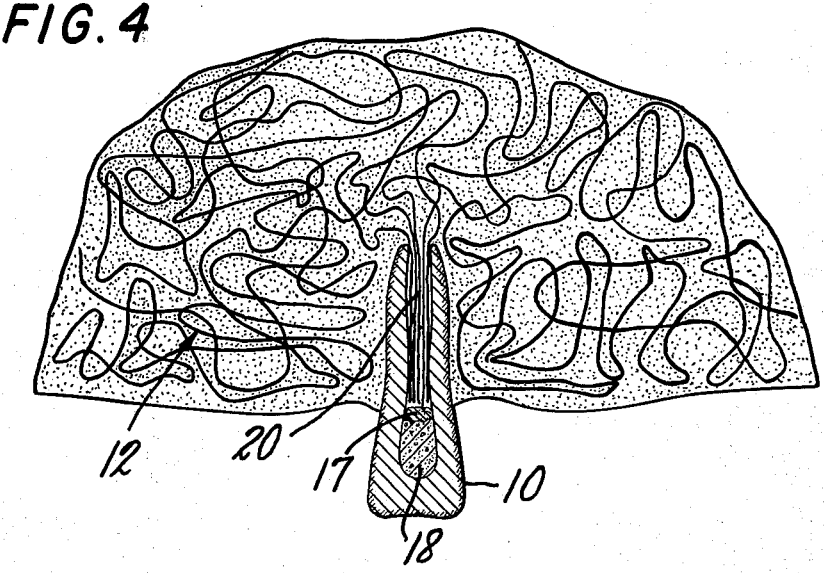
FIG. 4 is a diagrammatic showing of the final stages of the process of the present invention, with the solid plug of calcific tissue serving as a physiologic root canal seal.

FIG. 4 shows the final stages of the process of the present invention. This occurs within 3–6 months after the application of the gel and formation of the seal. Enzymatic depolymerization of the gel has taken place and ingrowth of connective tissue has calcified due to calcium phosphate crystals acting to seed the tissue.

were used to simulate the root canal of a pulpless endodontically treated tooth. Three series of mixtures as illustrated in Table I were prepared and were syringed into 22 tubes that had previously been heat-sealed at one end. All tubes were 10 millimeters in length with a 3.5 millimeter lumen diameter. Duplicate gel-filled tubes were first immersed in 37°C water for one-half hour resulting in setting of the gel and then implanted into dorsal subcutaneous connective tissues of adult Sprague-dawley rats. One empty tube and 3 tubes filled with a calcium hydroxide-saline paste were similarly placed as controls.

TABLE I

| Series No. | Collagen Gel | $CaCl_2$ | $K_2HPO_4$ | KI (5%) |
|---|---|---|---|---|
| 1 | 1.0 ml. | .05 ml. (40.5mM) | .05 ml. (36.1 mM) | .05 ml. |
| 2 | 1.0 ml. | .05 ml. (0.4 M) | .05 ml. (0.36 M) | none |
| 3 | 1.5 ml. | .05 ml. (2.0 M) | .05 ml. (1.8 M) | .05 ml. |

The solid plug 20 of the calcific tissue serves as a physiologic root canal seal.

The invention will be further described with reference to the following specific examples:

EXAMPLE I

It has been recognized that subcutaneous polyethylene tube implants in rats may be used to simulate non-vital open apex teeth; see Torneck, C. D.: Reaction of Rat Connective Tissue to Polyethylene Tube Implanting, O.S., O.M., O.P. 21:379 (1966). The composition and methods of the present invention were tested using subcutaneous tube implants in accordance with the following procedures.

MATERIALS AND METHODS

Lyophilized, highly purified calf skin collagen, which is non-antigenic and substantially free from mucopolysaccharides was obtained under the trade name Sigma C 3511, from the Sigma Co., St. Louis, Missouri. The material was reconstituted at a level of 10 mg/ml in 0.1 M acetate buffer with a pH of 3.5 at 4°C to produce a highly viscous gel. This gel was then dialized against a 0.115 M phosphate buffer with a pH of 7.6 at 4°C for 24 hours to raise the pH of the collagen to physiologic pH.

Solutions of $CaCl_2$ (40.5 mM, 0.4 M and 2.0 M) and $K_2HPO_4$ (36.1 mM, 0.36 M and 1.8 M) were prepared in Tris buffer at pH 7.4, Ionic strength I = 0.15 and the pH adjusted back to 7.4. The Tris buffer was obtained from Sigma Co., St. Louis, Mo., as Order No. T-1503. It was specified as a pH 7.4 buffer and is made from recrystalized primary standard gradt tris (hydroxymethyl) amino methane. It is blended with Trizma HCl or other compounds to obtain the precise buffer. Varying quantities of these preparations were mixed in equal amounts into the collagen to serve as the calcium and phosphate ion sources. The lowest of the three levels of salts used represent the physiologic level, while the other two levels are 10 and 50 fold increases over the physiologic level. A small quantity of 5% Lugol's solution (0.05 ml. per ml. of collagen) was added to half of the mixtures to speed gelation and serve as an antiseptic.

Subcutaneous polyethylene tube implants, similar to those used by Torneck in the reference given above Mixtures containing less calcium and phosphate than the mixtures of series 1 will result in decomposition of the gel, while mixtures containing more calcium than in the series 3 mixtures will result in denaturation of the collagen.

All animals were sacrificed at eight weeks. The implants were removed and placed in 10% neutral buffered formalin. Serial sections cut at 6 microns were prepared from each implant and stained with hematoxylin and eosin, Masson's trichrome and von Kossa stains.

RESULTS

Each tube, on gross inspection, was completely encapsulated in host connective tissue. Histologic examination showed the empty control tube to contain a thin connective tissue diaphragm whose fibers were continuous with those of the outer capsule. Specimens containing the calcium hydroxide displayed a slightly thicker band of tissue across the orifice with an amorphous calcific material deposited along the inner surface of the band. Few calcific particles were incorporated within the tissue.

Several of the mixtures of collagen-calcium phosphate gel produced dense fibrotic calcifying scars occluding the tube's orifices and ranging in thickness from 1.0 to 1.5 millimeters. Scar tissue quality varied in relation to collagen-calcium phosphate ratios and Lugol's solution content. The series 1 mixtures produced hypertrophic connective tissue scars with little or no calcification. The series 2 mixtures formed connective tissue scars which contained calcified or mineralized tissues. The series 3 mixtures caused calcification of the collagen gel and compaction and reorientation of the fibers within the gel. Microscopic examination showed the scars to contain dense bundles of host collagen fibers, fibroblasts and small amorphous calcific deposits. In two instances, von Kossa stain showed some of the host fiber bundles to be nucleating hydroxyapatite crystals. Foreign body response was usually mild, consisting primarily of lymphocytes and macrophages. Most scars demonstrated some degree of vascularization.

In addition to the above description, one of the series 3 mixtures produced an unusual result. A layer of a cellular calcified material was present within one of the two tubes, adjacent and inward to the connective tissue scar. Fibroblast-like cells demonstrating polarized nuclei were palisaded along this interface and appeared to be elaborating a new collagen matrix.

Tubes containing collagen gel containing no calcium phosphate both with and without Lugol's solution produced a thin diaphragm of connective tissue similar to that seen in the empty control tube.

Results of the test indicate that collagen gel in combination with various ionic strengths of minerals produce a greater mineralized scar formation than calcium hydroxide paste. Host connective tissue has migrated through this protein-mineral matrix as it compacted toward the tube's open end. This is in contrast to the impenetrableness of calcium hydroxide. The nucleation of minerals by host collagen fibers is strikingly similar to the epitaxy that occurs during early bone formation.

The various mixtures of collagen-calcium chloride and potassium phosphate, containing lugol's solution, were able to stimulate mineralized scar tissue formation and induce cellular differentiation.

The work with polyethylene tubes described above suggest that the gel formed by mixing collagen solution with calcium chloride, $K_2HPO_4$ and Lugol's solution when deposited apically in pulpless endodontically treated teeth, stimulates physiologic root end closure. This non-surgical technique enhances the prognosis and predictability in treatment of such cases.

EXAMPLE II

It has been recognized that the teeth of the rhesus monkey can be used as models for investigation of induced root apexification; Steiner, J. C. and von Hassel, H. J., Experimetal Root Apexification in Primates, *Oral Surg.* 31:409 (1971). The teeth of a 2 to 2½ year old rhesus monkey are considered appropriate models for the non-vital open apex teeth of an 8–10 year old child. Two mixtures of collagen, calcium chloride, potassium acid phosphate and Lugol's solution were tested on the teeth of the rhesus monkey in accordance with the following procedures.

Eight teeth of two healthy rhesus monkeys between two and two and one-half years old were selected for the test. The pulp from 6 teeth of one of the animals and two from the other animal was extirpated by use of an endodontic file. The file was passed through and beyond the apex of the teeth. The root canals were then irrigated with saline solution. The teeth were left open for one week and saliva was allowed to drain into the teeth.

After one week, the root canals of all eight teeth were again instrumented and irrigated with saline solution. A sample of the periapical tissue was tested for infection by use of a trypticase soy broth in 0.1% agar. The test was positive for all eight teeth. Without treating the infection, the canals were dried with paper points and three different compositions were placed into the root canals. A mixture (mixture IV) containing 1.0 ml. of the collagen solution of Example I, 0.05 ml. of 2.0 M $CaCl_2$ solution, 0.05 ml. of 1.8 M $K_2HPO_4$ solution and 0.05 ml. of the Lugol's solution was syringed into four of the teeth. A second mixture (mixture V) containing 1.0 ml. of collagen solution, 0.05 ml. of 0.4 $CaCl_2$ solution and 0.05 ml. of 0.36 M $K_2HPO_4$ solution was syringed into three other teeth, and a calcium hydroxide paste control was placed in the other tooth. Each tooth was then closed by applying a pre-fitted gutta percha cone approximately 4 mm. into the coronal portion of the root canal and then applying the dental cement.

X-rays of the teeth were taken at 6 and 12 weeks. At the end of 12 weeks, the animals were sacrificed and appropriate block sections of the jaw bones were removed. The block sections were fixed in 10% neutral buffered formalin. After two days, the sections were decalcified with Decal. The teeth were then put into dioxane for two more days. The teeth were removed from the dioxane and embedded in parafin wax. Then serial sections were made at approximately six microns. The serial sections were stained with hematoxylin and Masson's trichome stains.

Upon sacrifice, some blood was drawn from the left ventricle of the animals' hearts. This blood was tested for antibodies by the Ouchterlony test and by the ring or interfacial test.

RESULTS

The X-rays taken after six weeks showed that the collagen-calcium phosphate compositions were causing apexification of the root canal. After 12 weeks, the radiograph showed an even more complete deposition of cementum-like tissue.

The histologic tests on the serial sections indicated that cementum-like tissue had formed on the outer surfaces of the root canals and up to 3–4 mm. within the apical portion of the root canal. The results for both the mixtures IV and V were about equivalent. The fibers from the soft tissue within the canal were continuous with or embedded in the cementum-like deposition indicating a ligament-like attachment. This attachment within the canal was almost identical in appearance to the periodontal ligament attachment naturally occurring on the outside of the root which attaches the root to the bone.

The control tooth with calcium hydroxide paste demonstrated no physiologic closure. There appeared to be an attempt at hard tissue closure but the cementum-like tissue was irregular in shape and only on the outside of the tooth. Also, there was no hard or soft tissue ingrowth into the root canal.

The results of both the Ouchterlony test and the ring or interfacial test were negative. Thus, the introduction of the gel material did not cause the production of antibodies in the experimental animals, which normally are formed when a foreign object is introduced into the body.

These results indicate that the collagen-calcium phosphate gel composition produces a good physiologic and/or calcific plug of the apex of the root canal without producing the antibodies normally associated with the introduction of a foreign substance into the body.

I claim:
1. A method for causing formation of a physiologic seal across the opening of a rigid, cavity-containing tubular member adjacent capsular connective tissue within a mammalian body comprising
   a. filling the tube with a gelable composition comprising collagen, a calcium salt, and a phosphate salt,
   b. allowing the composition to gel, and
   c. permitting the ingrowth of connective tissue into the cavity.
2. The method of claim 1, wherein the gelable composition comprises collagen, $CaCl_2$, and $K_2HPO_4$.

3. The method of claim 1, wherein the gelable composition comprises collagen, $CaCl_2$, $K_2HPO_4$, and Lugol's solution.

4. The method of claim 1, wherein the gelable composition has a pH in the range of about 7.4 – 7.6 and comprises the following materials in the indicated respective proportions by volume:
   a. 1.0 – 1.5 ml. of a collagen solution containing from 10 mg. to 60 mg. of collagen in 1 ml. of aqueous buffered solution,
   b. 0.05 ml. of an aqueous $CaCl_2$ solution having a concentration ranging from 40.5 mM to 2.0 M, and
   c. 0.05 ml. of aqueous $K_2HPO_4$ ranging in concentration from 36.1 mM to 1.8 M.

5. The method of claim 4, wherein the composition additionally contains Lugol's solution in an amount sufficient to substantially decrease the gelling time of the composition.

6. The method of claim 5, wherein 0.05 ml. of aqueous 5% Lugol's solution is used.

7. A method for closing the root canal of a tooth comprising the steps of
   a. excising and removing dead and devitalized tissue from the canal,
   b. filling the canal with a composition comprising a buffered aqueous preparation of collagen, a calcium salt and a phosphate salt, and
   c. sealing the canal.

8. A method for inducing physiologic closure of a debrided open root canal of a tooth comprising the steps of
   a. opening the apical foramen thereof,
   b. filling the canal and adjacent opening in periapical tissue, if any, with a gelable composition comprising a buffered aqueous preparation of collagen, a calcium salt and a phosphate salt,
   c. sealing the canal, and
   d. permitting the ingrowth of connective tissue into the canal of the tooth, followed by mineralization to form a permanent physiologic closure.

9. The method of claim 8, wherein the composition is a high viscosity solution of collagen, calcium chloride and potassium phosphate, adjusted to pH 7.4.

10. The method of claim 9, wherein the composition has a pH in the range of about 7.4 – 7.6 and comprises the following materials in the indicated respective proportions by volume:
    a. 1.0 – 1.5 ml. of a collagen solution containing from 10 mg. to 60 mg. of collagen in 1 ml. of aqueous buffered solution,
    b. 0.05 ml. of an aqueous $CaCl_2$ solution having a concentration ranging from 40.5 mM to 2.0 M, and
    c. 0.05 ml. of aqueous $K_2HPO_4$ ranging in concentration from 36.1 mM to 1.8 M.

11. The method of claim 10, wherein the composition additionally contains 0.05 ml. of aqueous 5% Lugol's solution.

12. A composition for use in causing formation of a physiologic closure across the opening of a rigid tubular member adjacent capsular connective tissue within a mammalian body comprising an aqueous solution of collagen, a calcium salt, and a phosphate salt, the solution being buffered to a pH within the range of 7.4 – 7.6 and the solution forming a gel upon standing within about 30 minutes at about 37°C.

13. The composition according to claim 12, wherein the collagen is reconstituted lyophilized, highly purified calf skin collagen, which is non-antigenic.

14. The composition of claim 12, wherein the calcium salt is calcium chloride and wherein the phosphate salt is $K_2HPO_4$.

15. The method of making an endodontic composition comprising mixing at a pH range of about 7.4 – 7.6, the following materials in the indicated respective proportions by volume:
    a. 1.0 – 1.5 ml. of a collagen solution containing from 10 mg. to 60 mg. of collagen in 1 ml. of aqueous buffered solution,
    b. 0.05 ml. of an aqueous $CaCl_2$ solution having a concentration ranging from 40.5 mM to 2.0 M, and
    c. 0.05 ml. of aqueous $K_2HPO_4$ ranging in concentration from 36.1 mM to 1.8 M.

16. The method of claim 15, wherein the materials, after mixing, are placed within an applicator syringe and permitted to gel therein.

17. A gelable endodontic composition comprising the following materials in the indicated respective proportions by volume:
    a. 1.0 – 1.5 ml. of a collagen solution containing from 10 mg. to 60 mg. of collagen in 1 ml. of aqueous buffered solution,
    b. 0.05 ml. of an aqueous $CaCl_2$ solution having a concentration ranging from 40.5 mM to 2.0 M, and
    c. 0.05 ml. of aqueous $K_2HPO_4$ ranging in concentration from 36.1 mM to 1.8 M.

18. The endodontic composition in claim 17, wherein the composition additionally comprises sufficient Lugol's solution to substantially decrease the gelling time of the composition.

19. The composition of claim 17, which additionally comprises 0.05 ml. of aqueous 5% Lugol's solution.

20. An endodontic composition comprising 1.5 ml. of collagen solution containing 10 mg. collagen per ml. of water and having a pH of 7.6, 0.05 ml. of 2.0 M aqueous $CaCl_2$ solution buffered to pH 7.4, 0.05 ml. of 1.8 M aqueous $K_2HPO_4$ solution buffered to a pH of 7.4 and 0.05 ml. of aqueous 5% Lugol's solution.

* * * * *

UNITED STATES PATENT AND TRADEMARK OFFICE
CERTIFICATE OF CORRECTION

PATENT NO. : 3,968,567
DATED : July 13, 1976
INVENTOR(S) : Alan J. Nevins

It is certified that error appears in the above-identified patent and that said Letters Patent are hereby corrected as shown below:

Col. 3, line 67, "1.8" should be --1.8 M--;
Col. 5, line 4, "FIG. also" should be --Figure 3 also--;
Col. 5, lines 41 and 42, "Sigma C" should be --Sigma # C--;
Col. 5, line 55, "gradt" should be --grade--;
Col. 7, line 20, "lugol's" should be --Lugol's--;
Col. 7, line 64, "0.4 $CaCl_2$" should be --0.4 M $CaCl_2$--;
Claim 10, column 9, line 46, "composition has" should be --composition used has--;

Signed and Sealed this

Thirtieth Day of November 1976

[SEAL]

Attest:

RUTH C. MASON
Attesting Officer

C. MARSHALL DANN
Commissioner of Patents and Trademarks